United States Patent
Miyashita

[11] Patent Number: 5,252,742
[45] Date of Patent: Oct. 12, 1993

[54] SPIROPYRAN COMPOUNDS

[75] Inventor: Akira Miyashita, Ageo, Japan

[73] Assignee: Otsuka Kagaku Kabushiki Kaisha, Osaka, Japan

[21] Appl. No.: 13,171

[22] Filed: Jan. 29, 1993

Related U.S. Application Data

[63] Continuation of Ser. No. 602,234, Oct. 26, 1990, filed as PCT/JP90/00248, Feb. 27, 1990, abandoned.

[30] Foreign Application Priority Data

Feb. 28, 1989 [JP] Japan .................................. 1-48944
Feb. 28, 1989 [JP] Japan .................................. 1-48945

[51] Int. Cl.⁵ .................. C07D 293/10; C07D 209/96
[52] U.S. Cl. ................................ 548/121; 548/409
[58] Field of Search ............................... 548/121, 409

[56] References Cited

FOREIGN PATENT DOCUMENTS 2164684 7/1981 Japan ................................ 548/409

OTHER PUBLICATIONS

Kikuchi et al., Tokyo Institute of Technology, No. 7, (1972), pp. 1322–1330.

Primary Examiner—Alan Siegel
Attorney, Agent, or Firm—Armstrong, Westerman, Hattori, McLeland & Naughton

[57] ABSTRACT

The present invention provides a spiropyran compound represented by the formula

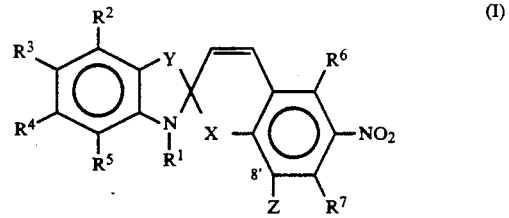

wherein $R^1$ is alkyl having 1 to 20 carbon atoms or aralkyl, $R^2$, $R^3$, $R^4$ and $R^5$ are the same or different and are each a hydrogen atom, alkyl having 1 to 6 carbon atoms, aryl or aralkyl, alkoxyl having 1 to 5 carbon atoms, halogen atom, cyano, trichloromethyl, trifluoromethyl or nitro, $R^6$ and $R^7$ are the same or different and are each a hydrogen atom, alkyl having 1 to 6 carbon atoms, aryl or aralkyl, halogen atom, cyano or nitro, X is an oxygen atom or sulfur atom, Y is Se or $(CH_3)_2C<$, Z is $$-CH_2OCC(CH_3)=CH_2,$$
$$\phantom{-CH_2O}\|\phantom{C(CH_3)=CH_2}$$
$$\phantom{-CH_2OCC(CH_3)}O$$

and X is a sulfur atom when Y is $(CH_3)_2C<$.

The spiropyran compound of the present invention itself is usable as a material such as recording material, photosensitive material, optical filter or decorative material. The present compound can further be homopolymerized or copolymerized with other polymerizable compound into a high polymer spiropyran compound for application to optical devices or dynamic devices.

12 Claims, 2 Drawing Sheets

SPIROPYRAN COMPOUNDS

This application is a continuation of application Ser. No. 602,234 filed Oct. 26, 1990, filed as PCT/JP90/00248, Feb. 27, 1990, now abandoned.

TECHNICAL FIELD

The present invention relates to spiropyran compounds.

BACKGROUND ART

Spiropyran derivatives are most well-known as typical organic compounds which reversibly colors or decolorizes upon exposure to the energy of light or heat. Examples and properties of these derivatives are collectively described, for example, in G. H. Brown, Photochromism (John Wiley & Sons, Inc., 1971).

However, attempts to introduce conventional spiropyran derivatives into use, for example, as recording media encounter the following problems.

(1) Since the colored form (or the colorless form) present in a solution or high polymer binder is low in stability to light or heat, the system immediately returns to colorless (colored). (2) When repeatedly exposed to light and heat for coloration and decolorization (recording and erasure), the exposure to light gives rise to a side reaction, which decomposes or deteriorates the spiropyran derivative. Thus, the derivative is not fully resistant to repetitions. (3) Although the spiropyran derivative for use as a photochromic medium is usually dispersed in a high polymer substance, the derivative dissolves out from the high polymer substance, or separates out therefrom through phase separation since the derivative generally has low compatibility with the high polymer substance.

An object of the present invention is to provide a novel spiropyran compound capable of easily giving a high polymer spiropyran compound which is usable free of the drawbacks of the conventional photochromic materials.

DISCLOSURE OF THE INVENTION

The present invention provides a spiropyran compound represented by the formula

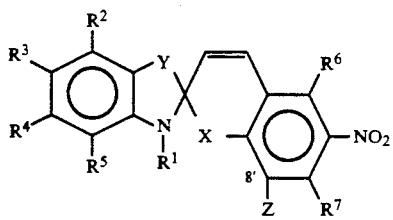 (I)

wherein $R^1$ is alkyl having 1 to 20 carbon atoms or aralkyl, $R^2$, $R^3$, $R^4$ and $R^5$ are the same or different and are each a hydrogen atom, alkyl having 1 to 6 carbon atoms, aryl or aralkyl, alkoxyl having 1 to 5 carbon atoms, halogen atom, cyano, trichloromethyl, trifluoromethyl or nitro, $R^6$ and $R^7$ are the same or different and are each a hydrogen atom, alkyl having 1 to 6 carbon atoms, aryl or aralkyl, halogen atom, cyano or nitro, X is an oxygen atom or sulfur atom, Y is Se or $(CH_3)_2C<$, Z is

and X is a sulfur atom when Y is $(CH_3)_2C<$.

The compound of the present invention is expected for use in the fields of high-density optical recording materials, optical filters, image forming materials, photosensitive materials, nonlinear optical devices and conversion of optical energy to dynamic energy.

The compound of the invention can be made into a high polymer spiropyran compound having a desired structure and desired spiropyran content when polymerized singly or copolymerized with a desired polymerizable compound as required.

The compound of the invention is free of the foregoing drawbacks of the conventional spiropyran derivatives. When introduced into the main chain of a high polymer through a chemical bond, the present compound is expected to exhibit the following advantages.

(1) The compound is given improved stability and becomes less likely to dissolve out from the high polymer substance. In addition, (2) the high polymer substance is by itself usable for forming a film or like medium having photochromism. Furthermore, the present compound, when chemically bonded to a high polymer chain, makes it possible to optically reversibly control the structure of the high polymer compound and the properties thereof such as polarity, viscosity and solubility.

The compound of the present invention exhibits photochromism and is itself usable as an optical material for various purposes. The present compound further affords a high polymer spiropyran compound when homopolymerized or copolymerized with a desired polymerizable compounds as required. Application to various uses is expected of the polymer obtained as a photoresponsive polymer.

Since the compound of the present invention has a methacryloxymethyl group at the 8'-position of its spiropyran skeleton, the spiropyran compound can be introduced into the main chain of a high polymer by polymerization through a chemical bond. This imparts improved stability to the spiropyran compound and also overcomes the above problem that spiropyran derivatives will dissolve or separate out form high polymer substances. Moreover, the polymer is singly usable for forming a photoresponsive film or like medium, or is usable as a photoresponsive high polymer compound which can be made into a substance adapted to optically reversibly exhibit an altered structure or polarity, viscosity, solubility or like property.

The compound of the present invention is a benzoselenazoline spirobenzopyran, benzoselenazoline spirobenzothiopyran or indoline spirobenzothiopyran and is characterized in that the compound has a methacryloxymethyl group at the 8'-position of the spirobenzopyran skeleton or spirobenzothiopyran.

Spirobenzopyran compounds having a substituent on a polymerizable side chain are disclosed, for example, in Nippon Kagaku Kaishi, 1323 (1972), J. Polym. Sci. Polym. Chem. Ed., 12, 2511 (1974), JP-A-88895/1978, JP-A-227972/1984, JP-A-76490/1986, etc., whereas the disclosed compounds are all indoline or benzothiazoline spiropyran compounds which are different from the compound of the invention in chemical structure.

Among the compounds of the present invention, those wherein Y is Se have the feature of exhibiting so-called reverse photochromism such that they are usually (at room temperature) colored which disappears when exposed to visible light and restore the original color when exposed to ultraviolet rays or heated. Further the spiropyran compounds of the invention having the above-mentioned specific group at the 8'-position also have the feature of exceedingly greater in molecular extinction coefficient ($\epsilon$ value) than the compounds of the formula (II) below wherein the 8'-position is unsubstituted.

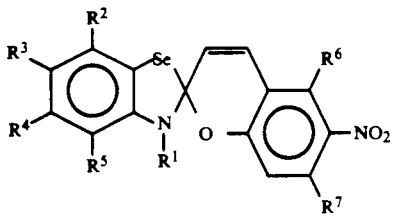

(II)

wherein $R^1$, $R^2$, $R^3$, $R^4$, $R^5$, $R^6$ and $R^7$ are as defined above.

In the formula representing the spiropyran compounds of the present invention, examples of alkyl groups are methyl, ethyl, propyl, isopropyl, butyl, hexyl, decyl, tetradecyl, octadecyl and eicosyl; examples of aralkyl groups are phenyl $C_{1\sim6}$ alkyl groups which may have on the benzene ring 1 to 5 substituents such as $C_{1\sim6}$ alkyl groups, $C_{1\sim6}$ alkoxyl groups, halogens atoms, cyano groups, trichloromethyl groups, trifluoromethyl groups on nitro groups; examples of aryl groups are phenyl and naphthyl groups which may have 1 to 5 substituents such as $C_{1\sim6}$ alkyl groups, $C_{1\sim6}$ alkoxyl groups, halogen atoms, cyano groups, trichloromethyl groups, trifluoromethyl groups or nitro groups; examples of alkoxyl groups are methoxy, ethoxy, propoxy, butoxy and pentyloxy; and examples of halogen atoms are fluorine atom, chlorine atom, bromine atom and iodine atom.

The compound of the invention represented by the formula (I) can be easily prepared from a quaternary ammonium salt derivative represented by the formula (III) and a 5-nitrobenzaldehyde derivative represented by the formula (IV) by subjecting these derivatives to condensation in the presence of an amine as represented by the following reaction scheme.

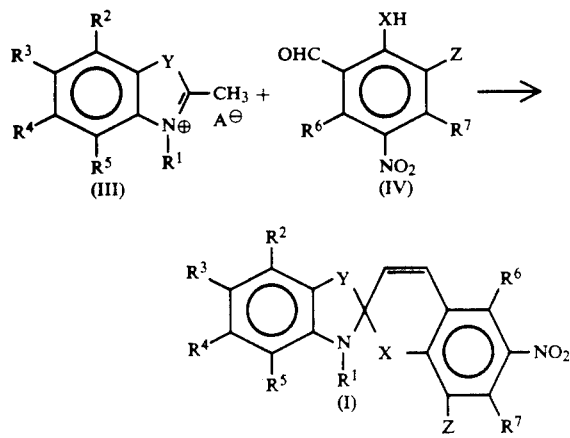

wherein $R^1$, $R^2$, $R^3$, $R^4$, $R^5$, $R^6$, $R^7$, X, Y and Z are as defined above, and A is a halogen atom such as chlorine, bromine or iodine or $R^8SO_3$, $R^8$ being methyl, ethyl or like lower alkyl group, or phenyl, chlorophenyl, methylphenyl or like aromatic group.

Among the compounds of the formula (III) useful as starting materials, those wherein Y is Se, i.e., quaternary benzoselenazolenium salt derivatives, can be prepared by reacting a corresponding 2-methylbenzoselenazole derivative with a compound of the formula $R^1A$ (wherein $R^1$ and A are as defined above) in an amount of at least 1 mole, preferably 1.05 to 1.5 moles, per mole of the derivative at about 50° to about 100° C. for about 0.1 to about 50 days. The 2-methylbenzoselenazole derivative is a known compound disclosed, for example, in Ber. 46, 94 (1913), J. Amer. Chem. Soc., 68 1536 (1946) or British Patent 1,411,957 (1975), or can be prepared by the process disclosed in these publications. Among the compounds of the formula (III) for use as starting materials, those wherein Y is $(CH_3)_2C<$, i.e., quaternary indolenium salt derivatives, can be prepared by reacting a corresponding 2,3,3-trimethylindolenine derivative with a compound of the formula R'A (wherein A is as defined above) in an amount of at least 1 mole, preferably 1.05 to 1.5 moles, per mole of the derivative at about 20° to about 100° C. for about 1 to about 48 hours.

On the other hand, 5-nitrobenzaldehyde derivatives represented by the formula (IV) are prepared, for example, by reacting a salicylaldehyde derivative represented by the formula (V)

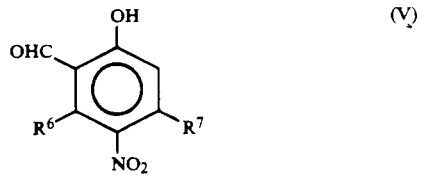

(V)

wherein $R^6$ and $R^7$ are as defined above with chloromethyl methyl ether to obtain a 3-chloromethyl-5-nitrosalicylaldehyde derivative represented by the formula (VI)

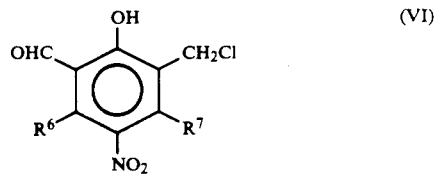

(VI)

wherein $R^6$ and $R^7$ are as defined above, and subsequently reacting silver methacrylate with the compound of the formula (VI) to obtain a 3-methacryloxymethyl-5-nitrosalicylaldehyde derivative represented by the formula (VII)

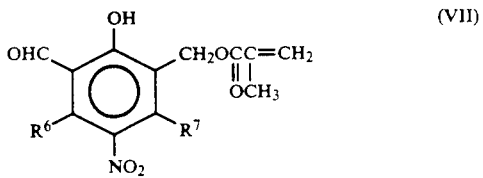

(VII)

wherein R⁶ and R⁷ are as defined above. The resulting derivative is a compound of the formula (IV) wherein X is O.

The compound of the formula (IV) wherein X is S is prepared by reacting N,N-dimethylthiocarbamoyl chloride with the resulting compound of the formula (IV), for example, in the same manner as is disclosed in J P-A-54388/1985 to obtain a 2-O-(N,N-dimethylthiocarbamoyl)benzaldehyde derivative represented by the formula (VII)

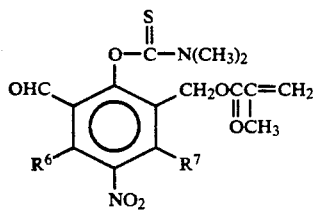
(VIII)

wherein R⁶ and R⁷ are as defined above, then heating the derivative for isomerization to obtain 2-S-(N,N-dimethylthiocarbamoyl)benzaldehyde derivative represented by the formula (IX)

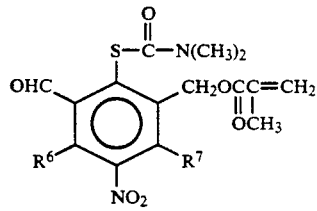
(IX)

wherein R⁶ and R⁷ are as defined above, and subsequently hydrolyzing the derivative with an alkali.

The reaction between the quaternary ammonium salt derivative of the formula (III) and the 5-nitro-benzaldehyde derivative of the formula (IV) is effected by dissolving the two derivatives in a suitable solvent, adding an amine to the solution at room temperature to the boiling point of the solvent and heating the mixture for 1 to 24 hours. It is desirable to use about 0.9 to about 1.1 moles of the compound of the formula (III) per mole of the compound of the formula (IV). Examples of solvents suitable for use are those capable of dissolving the compounds of the formulae (III) and (IV), such as methanol, acetone, methyl ethyl ketone, ethyl acetate, butyl acetate, dichloromethane, dimethylformamide and the like. Amines suitable for use are piperidine, morpholine, triethylamine, pyridine, lutidine, 1,4-diazabicyclo [2.2.2]octane, 1,5-diazabicyclo [4.3.0]nonene, 1,8-diazabicyclo[5.4.0] undecene and the like. The amine is used in an amount of about 1 to about 10 moles per mole of the compound of the formula (III).

The spirobenzopyran compound represented by the formula

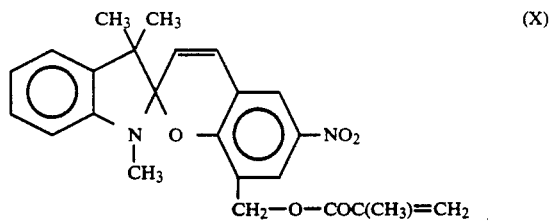
(X)

is disclosed, for example, in Nippon Kagaku Kaishi 1323 (1972) as a compound analogous to the compounds of the invention wherein X is S and Y is $(CH_3)_2C<$. Investigations are under way on the photochromic characteristics of polymers obtained by polymerizing the compound.

However, although it is generally though that colored form exhibits enhanced stability when highly polymerized, the colored species prepared, for example, by copolymerizing the compound with styrene is very unstable and is as short as about 1 minute in half-life. Thus, the substance immediately reverts to a stable state (loses color) at room temperature, hence a serious drawback for use as a photoresponsive material.

Unlike the above compound, the compound of the invention exhibits high stability when serving as a colored form and high stability to repetitions of coloration and decolorization, and can be given further enhanced stability when highly polymerized.

The compounds of the invention represented by the formula (XI) below can be easily prepared also by reacting a 2-methylene-3,3-dimethylindolenine derivative represented by the formula (XII) with a 5-nitrothiosalicylaldehyde derivative represented by the formula (XIII) with heating as shown by the following reaction scheme.

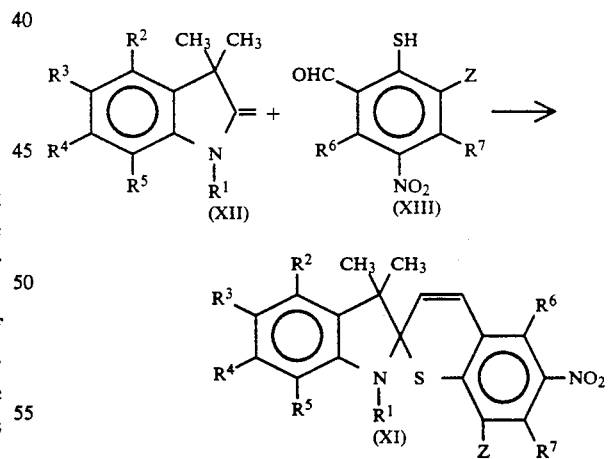

wherein $R^1$, $R^2$, $R^3$, $R^4$, $R^5$, $R^6$, $R^7$ and Z are as defined above.

The compounds of the present invention thus obtained can be easily isolated from the reaction mixture and purified by conventional separation and purification methods.

BEST MODE OF CARRYING OUT THE INVENTION

Figure 1:
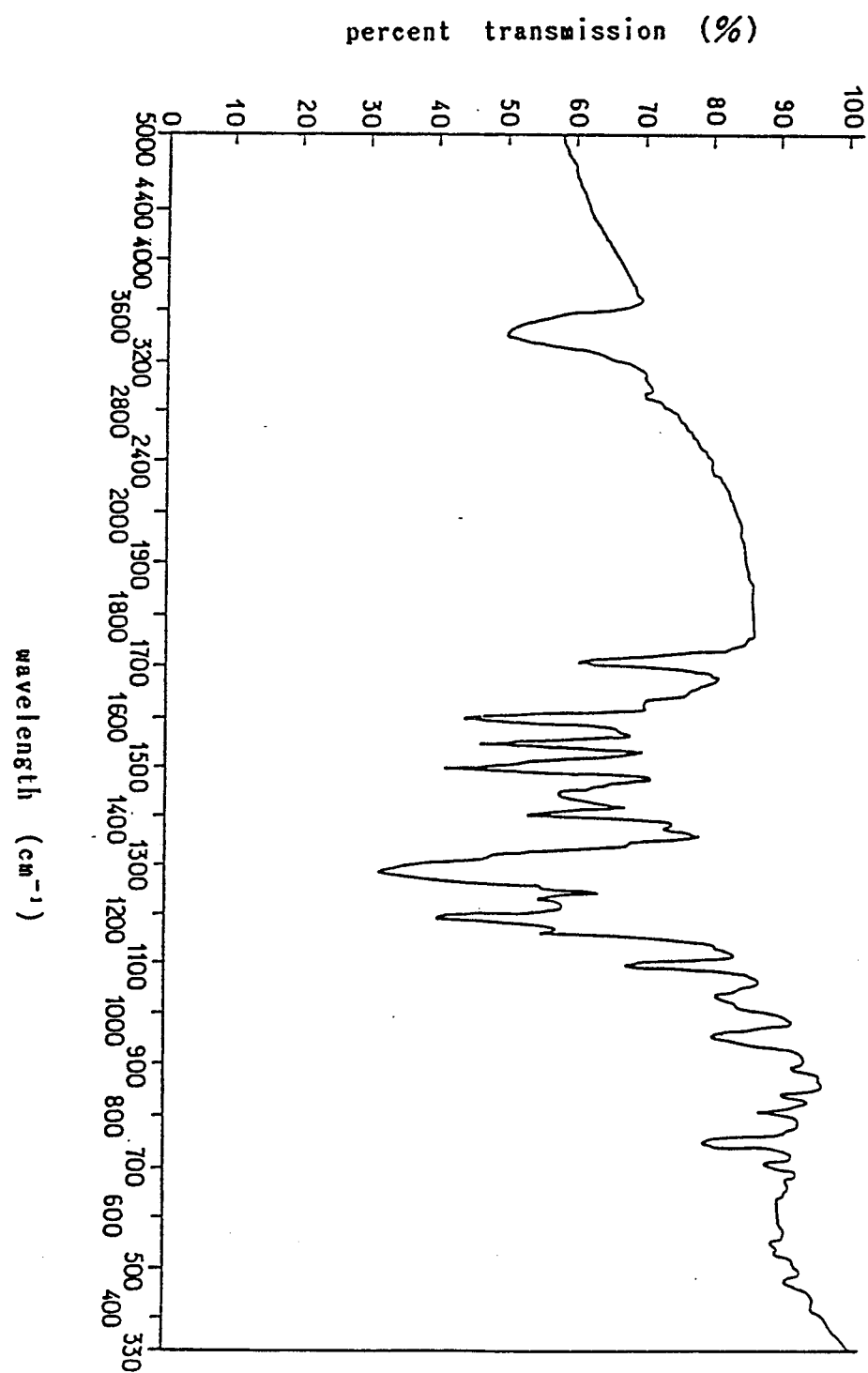
FIG. 1 shows an I R spectrum of the compound obtained in Example 4.

Examples are given below for a better understanding of the present invention.

EXAMPLE 1

While cooling a mixture of 12.0 g of 5-nitrosalicylaldehyde and 100 ml of chloromethyl methyl ether in an ice bath, 43.9 g of anhydrous aluminum chloride was added in small portions to the mixture, followed by stirring at room temperature for 10 minutes and thereafter by refluxing with heating for 22 hours. The reaction mixture was then cooled in an ice bath, and 200 ml of water was added to the mixture with full stirring, whereby white crystals were separated out. The white crystals were collected and dissolved in hot hexane, and the solution was filtered. The mother liquor was thereafter cooled, giving 14.9 g of 3-chloromethyl-5-nitrosalicylaldehyde in the form of white needlelike crystals (yield 72%).

$^1$H-NMR(CDCl$_3$); δppm 4.72(s, 2H, —CH$_2$Cl), 8.56(s, 2H, ArH), 10.00(s, 1H, CHO), 12.10(s, 1H, OH).

EXAMPLE 2

A 10.5 g quantity of 3-chloromethyl-5-nitrosalicylaldehyde was dissolved in 100 ml of toluene, and 11.4 g of silver methacrylate was added to the solution. The mixture was heated at 120° C. for 2.5 hours and then cooled to room temperature. The resulting precipitate was removed by filtration. The toluene solution obtained was concentrated under reduced pressure, giving 12.7 g of 3-methacryloxymethyl-5-nitrosalicylaldehyde in the form of a pale yellow powder (yield 98%).

$^1$H-NMR (CDCl$_3$); δppm 2.00(t, 3H, CH$_3$), 5.34(s, 2H, —CH$_2$—), 5.67(t, 1H, vinyl), 6.22(m, 1H, vinyl), 8.53(m, 2H, ArH), 10.00(s, 1H, CHO).

EXAMPLE 3

A 10.1 g quantity of 2-methylbenzoselenazole was dissolved in 100 mg of chloroform, and the solution was heated with addition of 10.0 g of methyl iodide in an autoclave at 80° C. for 5 days. The crystals produced by the reaction were collected by filtration, washed with ether and then dried, affording 16.4 g of 2,3-dimethylbenzoselenazolenium iodide (yield 94%).

$^1$H-NMR (D$_2$O); δppm 3.13(s, 3H, 2-methyl), 4.16(s, 3H, 3-methyl), 7.73(t, 1H, ArH), 7.83(d, 1H, ArH), 8.13(d, 1H, ArH), 8.15(s, 1H, ArH).

EXAMPLE 4

To 200 ml of methanol were added 10.6 g of 3-methacryloxymetyl-5-nitrosalicylaldehyde and 13.6 g of 2,3-dimethylbenzoselenazolenium iodide. While refluxing the mixture with heating, a solution of 34.2 g of piperidine in 50 ml of methanol was added dropwise in small portions to the mixture. After continued refluxing with heating for 27 hours, the reaction mixture was cooled to room temperature. The resulting brown crystals were separated off, giving 18.0 g of 8'-methacryloxymethyl-3-methyl-6'-nitro-1-selenaspiro-[2H-1'-benzopyran-2,2'-benzoselenazoline] (yield 100%).

$^1$H-NMR (DMSO); δppm 1.91(s, 3H, methacryl—CH$_3$), 4.10(s, 3H, N—CH$_3$), 5.03(s, 2H, —CH$_2$—), 5.70(s, 1H, vinyl), 6.06(s, 1H, vinyl), 7.58(t, 1H, 6-H), 7.71(t, 1H, 5-H), 7.90(d, 1H, 3'-H), 8.05(d, 1H, 4-H), 8.17(d, 1H, 7'-H), 8.32(d, 1H, 7-H), 8.53(d, 1H, 4'-H), 8.70(d, 1H, 5'-H).

FIG. 1 shows an IR spectrum of the compound obtained.

EXAMPLE 5

Figure 2:
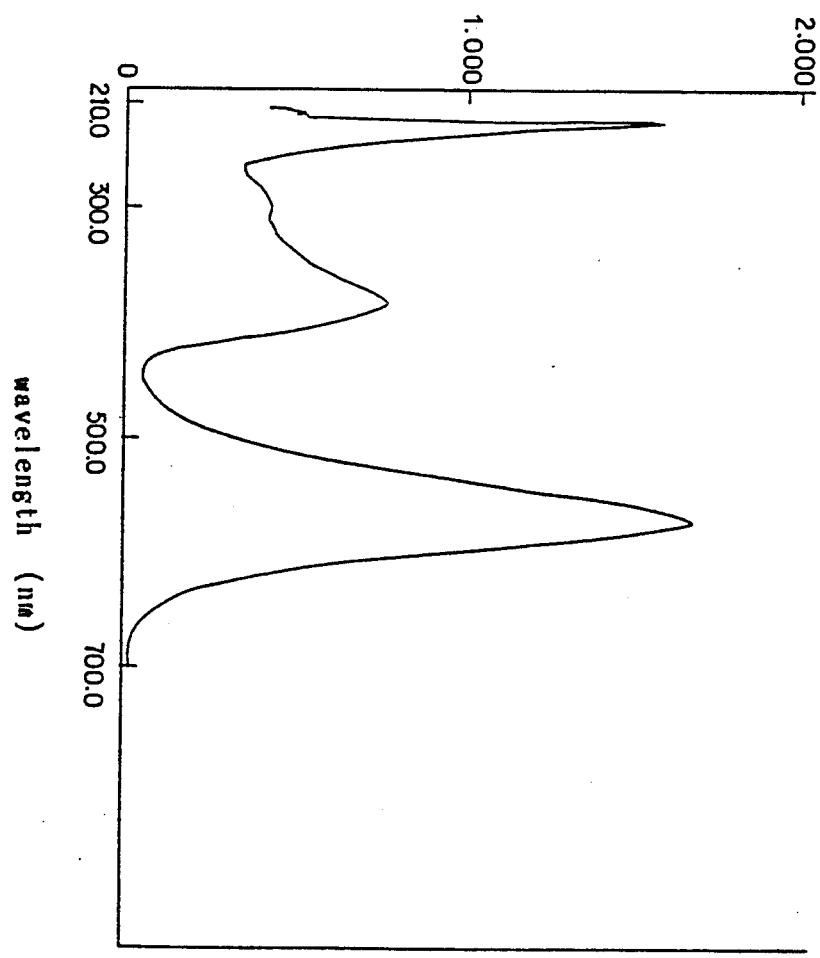
FIG. 2 shows an absorption spectrum of the solution of Example 5 when the recoloration reached an equilibrium.

The photochromic characteristics of the compound obtained in Example 4 were determined. A methylene chloride solution (bluish purple) of the compound was irradiated with visible light using a 500-W extra-high pressure mercury lamp equipped with a cutoff filter for passing visible light of at least 500 nm, whereby the solution was turned colorless. The colorless solution became bluish purple again when maintained at 24° C. FIG. 2 shows an absorption spectrum of the solution when the state of recoloration reached an equilibrium.

The result indicates that the compound exhibited reverse photochromism, λmax=571 nm. The molecular extinction coefficient ε at this wavelength was 23,000.

On the other hand, the colored solution as maintained at 0° C. was irradiated with the same visible light as above for 1 minute to obtain a colorless transparent solution, which was extremely stable at this temperature, and exhibited no recoloration and remained colorless even after the lapse of 6 hours. When the colorless solution was irradiated at 0° C. with ultraviolet rays for 1 minute using a 500-W extra-high pressure mercury lamp equipped with a cutoff filter for passing ultraviolet rays around 350 nm, the solution turned bluish purple again. When the solution was repeatedly subjected to 100 cycles of photo erasure with visible light and recoloration with ultraviolet rays, the solution repeatedly reproduced the color without any decrease in the absorbance in the state of recoloration.

The methylene chloride solution, which was bluish purple at room temperature, was irradiated at 0° C. with visible light in the same manner as above and thereby changed into a colorless transparent solution, which was then maintained at 25° C., whereby the solution was restored to the original bluish purple transparent solution. This cycle was repeatable at least 30 times with reproducibility without any decrease in the absorbance in the state of the colored form, and the solution was still in condition for many repetitions of the cycle.

EXAMPLE 6

To 50 ml of methanol were added 3.66 g of 3-isopropyl-2-methylbenzoselenazolenium iodide separately prepared and a 2.66 g portion of the 3-methacryloxymethyl-5-nitrosalicylaldehyde previously prepared. While heating the mixture under reflux, a solution of 0.86 g of piperidine in 10 ml of methanol was added dropwise in small portions to the mixture. The mixture was then reacted and treated in the same manner as in Example 4, giving 4.51 g of 3-isopropyl-8'-methacryloxymethyl-6'-nitro-1-selenaspiro-[2H-1'-benzopyran-2,2'-benzoselenazoline] (formula XIV) in a yield of 93%.

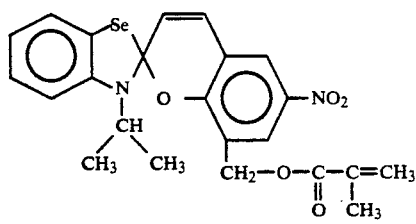
(XIV)

MS(70 eV); 486(M+),

IR(KBr); 3045~3090, 1728, 1598, 1561, 1490, 1325 cm⁻¹.

The chloroform solution of the product was purple at room temperature (24° C.), and λmax=615 nm.

When the product was tested by two methods of repeating coloration and decolorization in the same manner as in Example 5, the product exhibited high reproducibility similarly without any decrease in absorbance,

EXAMPLE 7

To 50 ml of methanol were added 3.96 g of 3-isopropyl-5-methoxy-2-methylbenzoselenazolenium iodide prepared separately and a 2.66 g portion of the 3-methacryloxymethyl-5-nitrosalicylaldehyde. While heating the mixture under reflux, a solution of 0.86 g of piperidine in 10 ml of methanol was added dropwise in small portions to the mixture. When reacted and treated in the same manner as in Example 4, the mixture gave 4.63 g of 3-isopropyl-8'-methacryloxymethyl-5-methoxy-6'-nitro-1-selenaspiro[2H-1'-benzopyran-2,2'-benzoselenazoline] (formula XV) in a yield of 90%.

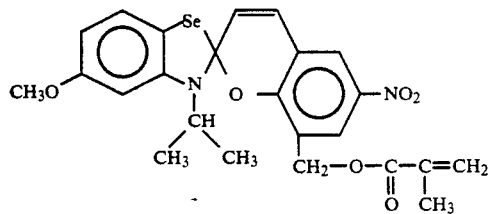
(XV)

MS (70 eV); 516(M+),

IR(KBr); 3010~3085, 1735, 1605, 1560, 1498, 1320 cm⁻¹.

The chloroform solution of the product was purple at room temperature (24° C.), and λmax=640 nm.

When the product was tested by two methods of repeating coloration and decolorization in the same manner as in Example 5, the product exhibited high reproducibility similarly without any decrease in absorbance.

EXAMPLE 8

Into a sealed tube were placed 2.26 g of 5-methoxy-2-methylbenzoselenazole, 1.93 g of methyl p-toluenesulfonate and 10 ml of chloroform, which were made into a uniform solution and then heated at 100° C. for 2 days. The reaction mixture was concentrated, and the residue was washed with ether and then dried under reduced pressure, giving 4.07 g of 5-methoxy-2,3-dimethylbenzoselenazolenium p-toluenesulfonate in the form of a purple powder (yield 99%).

¹H-NMR(D₂O); δppm 2.4(s, 3H, CH₃Ar), 3.2(s, 3H, 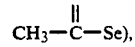

4.0(s, 3H, CH₃O), 4.1(s, 3H, CH₃N), 7.2~8.1(m, 7H, ArH).

EXAMPLE 9

Into a reactor with the inside air replaced by nitrogen were placed 0.80 g of 3-methacryloxymethyl-5-nitrosalicylaldehyde, 1.25 g of 5-methoxy-2,3-dimethylbenzoselenazolenium p-toluenesulfonate and 15 ml of methanol, which were made into a uniform solution. A solution of 0.28 g of piperidine in 5 ml of methanol was added to the solution, and the mixture was heated under reflux for 20 hours. The reaction mixture was cooled to room temperature, and the resulting dark purple crystals were separated off by centrifuging, washed with methanol and then dried in a vacuum, giving 1.40 g of 8'-methacryloxymethyl-5-methoxy-2-methyl-6'-nitro-1-selenaspiro [2H-1'-benzopyran-2,2'-benzoselenazoline] (yield 96%).

¹H-NMR (DMSO); δppm 1.91(s, 3H, methacryl—CH₃), 3.89(s, 3H, O—CH₃), 4.07(s, 3H, N—CH₃), 5.06(s, 2H, —CH₂—), 5.70(s, 1H, vinyl), 6.05(s, 1H, vinyl), 7.17(dd, 1H, 6-H), 7.50(d, 1H, 4-H), 7.83(d, 1H, 5' or 7'-H), 8.05(d, 1H, 3' or 4'-H), 8.12(d, 1H, 7-H), 8.42(d, 1H, 7' or 5'-H), 8.64(d, 1H, 4' or 3'-H).

MS (70 eV); 487(M+).

The chloroform solution of the product was purple at room temperature (23° C.), and λmax=587 nm. The molecular extinction coefficient ε at this wavelength was 33000.

When the product was tested by two methods of repeating coloration and decolorization in the same manner as in Example 5, the product exhibited high reproducibility similarly without any decrease in absorbance.

EXAMPLE 10

A 4.20 g quantity of 2,5-dimethylbenzoselenazole, 3.90 g of methyl p-toluenesulfonate and 20 ml of chloroform were placed into a sealed tube, and reacted and treated in the same manner as in Example 8, giving 7.62 g of 2,3,5-trimethylbenzoselenazolenium p-toluenesulfonate in the form of a pink powder (yield 96%).

NMR (D₂O); δppm 2.2(s, 3H, CH₃Ar), 2.6(s, 3H, 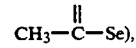

3.2(s, 3H, CH₃—N), 7.1~8.1(m, 7H, Ar—H).

EXAMPLE 11

Into a reactor with the inside air replaced by nitrogen were placed 0.80 g of 3-methacryloxymethyl-5-nitrosalicylaldehyde, 1.20 g of 2,3,5-trimethylbenzoselenazolenium p-toluenesulfonate and 15 ml of methanol, which were made into a uniform solution. A solution of 0.28 g of piperidine in 5 ml of methanol was added to the solution, and the mixture was heated under reflux for 24 hours. The reaction mixture was cooled to room temperature, and the resulting dark purple crystals were separated off by centrifuging, washed with methanol and then dried in a vacuum, giving 1.39 g of 2,5-dimethyl-8'-methacryloxymethyl-6'-nitro-1-selenaspiro [2H-1'-benzopyran-2,2'-benzoselenazoline] (yield 98%).

$^1$H-NMR (DMSO); δppm 1.91(s, 3H, methacryl—CH$_3$), 2.49(s, 3H, 5—CH$_3$), 4.05(s, 3H, N—CH$_3$), 5.02(s, 2H, —CH$_2$—), 5.70(s, 1H, vinyl), 6.06(s, 1H, vinyl), 7.36(d, 1H, 6-H), 7.83(s, 1H, 4-H), 7.84(d, 1H, 5' or 7'-H), 8.06(d, H, 3' or 4'-H), 8.13(d, 1H, 7-H), 8.41(d, 1H, 7' or 5'-H), 8.65(d, 1H, 4' or 3'-H), MS(70 eV); 471(M+), The chloroform solution of the product was purple at room temperature (23° C.), and λmax=579 nm. The molecular extinction coefficient ε at this wavelength was 23000.

When the product was tested by two methods of repeating coloration and decolorization in the same manner as in Example 5, the product exhibited high reproducibility similarly without any decrease in absorbance.

EXAMPLE 12

In 300 ml of dimethylformamide were dissolved 13.8 g of 3-methacryloxymethyl-5-nitrosalicylaldehyde and 11.2 g of 1,4-diazabicyclo[2.2.2]octane, and the solution was heated to 50° C. A solution of 12.9 g of N,N-dimethylthiocarbamoyl chloride in 50 ml of dimethylformamide was slowly added to the solution, followed by heating at 50° C. for 2 hours. Water (80 ml) was added to the reaction mixture, and the resulting mixture was subjected to extraction with ethyl acetate. The extract was washed with saturated sodium chloride solution and concentrated under reduced pressure, giving 17.6 g of 2-O-(N,N-dimethylthiocarbamoyl)-3-methacryloxymethyl-5-nitrobenzaldehyde (crude yield 96%).

$^1$H-NMR(CDCl$_3$); δppm 2.0(m, 3H, CH$_3$), 3.5(d, 6H, N—CH$_3$), 5.3(d, 2H, —CH$_2$—), 5.7(m, 1H, vinyl), 6.2(m, 1H, vinyl), 8.6(d, 1H, ArH), 8.7(d, 1H, ArH), 10.0(s, 1H, CHO),

EXAMPLE 13

A mixture of 12.6 g of 2-O-(N,N-dimethylthiocarbamoyl)-3-methacryloxymethyl-5-nitrobenzaldehyde and 100 ml of ethanol was heated under reflux for 21 hours. The reaction mixture was concentrated under reduced pressure, and the resulting residue was dried in a vacuum and purified by a silica gel column, affording 10.7 g of 2-S-(N,N-dimethylthiocarbamoyl)-3-methacryloxymethyl-5-nitrobenzaldehyde (yield 85%).

$^1$H-NMR(CDCl$_3$); δppm 2.0(s, 3H, CH$_3$), 3.1(d, 6H, N—CH$_3$), 5.5(s, 2H, —CH$_2$—), 5.7(m, 1H, vinyl), 6.2(m, 1H, vinyl), 8.6(d, 1H, ArH), 8.7(d, 1H, ArH), 10.3(s, 1H, CHO).

IR(KBr); 1720, 1690, 1660, 1535, 1345 cm$^{-1}$,

EXAMPLE 14

To a mixture solution of 14.1 g of 2-S-(N,N-dimethylthiocarbamoyl)-3-methacryloxymethyl-5-nitrobenzaldehyde and 200 ml of methanol was added 140 ml of 0.64N aqueous solution of sodium hydroxide at room temperature. The reaction mixture was then acidified to a pH value of 2 with addition of 380 ml of 0.49N hydrochloric acid and thereafter concentrated under reduced pressure. The residue obtained was subjected to extraction with ether, and the extract was washed with water and concentrated under reduced pressure, affording 9.79 g of 3-methacryloxymethyl-5-nitrothiosalicylaldehyde in the form of orange crystals (yield 87%).

$^1$H-NMR(CDCl$_3$); δppm 2.0(m, 3H, CH$_3$), 5.3(s, 2H, —CH$_2$—), 5.7(m, 1H, vinyl), 6.2(m, 1H, vinyl), 8.4(m, 2H, ArH), 10.1(s, 1H, CHO).

EXAMPLE 15

To a solution of 16.0 g of 2,3,3-trimethylindolenine in 100 ml of chloroform was added 15.9 g of methyl iodide, and the mixture was heated at 80° C. for 21 hours in an autoclave. The resulting precipitate was separated off by filtration to obtain 27.5 g of 1,2,3,3-tetramethylindolenium iodide in the form of white crystals. With addition of 270 ml of 10N aqueous solution of potassium hydroxide, the product was heated in a nitrogen atmosphere at 50° C. for 2.5 hours. The reaction mixture was then subjected to extraction with ether, and the extract was dried over magnesium sulfate and thereafter concentrated under reduced pressure, giving 14.1 g of 2-methylene-1,3,3-trimethylindoline (yield 81%).

$^1$H-NMR(CDCl$_3$); δppm 1.3(s, 6H, CH$_3$), 3.0(s, 3H, N—CH$_3$), 6.5~7.0(dd, 2H, vinyl), 7.0~7.2(m, 4H, ArH).

EXAMPLE 16

In 120 ml of 2-butanone were dissolved 14.1 g of 3-methacryloxymethyl-5-nitrothiosalicylaldehyde and 8.7 g of 2-methylene-1,3,3-trimethylindoline, and the solution was heated under reflux for 20 hours in a nitrogen atmosphere. The reaction mixture was concentrated under reduced pressure, and the residue was purified by a silica gel column, giving 15.9 g of 8-methacryloxymethyl-6-nitro-1',3',3'-trimethylspiro[2H-1-benzothiopyran-2,2'-indoline] in the form of pale yellow crystals (yield 73%).

$^1$H-NMR(CDCl$_3$); δppm 1.24(s, 3H, CH$_3$), 1.39(s, 3H, CH$_3$), 1.97(d, 3H, CH$_3$), 2.67(s, 3H, N—CH$_3$), 5.15(dd, 2H, CH$_2$), 5.62(t, 1H, vinyl), 6.05(d, 1H, thiopyran), 6.16(s, 1H, vinyl), 6.51(d, 1H, thiopyran), 6.65(t, 1H, indoline), 6.96(d, 1H, indoline), 7.06(d, 1H, indoline), 7.17(t, 1H, indoline), 8.02(d, 1H, benzothiopyran), 8.08(d, 1H, benzothiopyran).

EXAMPLE 17

The product obtained in Example 16 was dissolved in a solvent, and the solution was irradiated with ultraviolet rays using an extra-high pressure mercury lamp (USHIO USH-500 D) equipped with a band filter for passing ultraviolet rays around 350 nm, whereby the solution, which was colorless and transparent, was changed to a green solution. In methanol, the maximum absorption wavelength λmax was 588 nm. The half-life of the colored form was 15 minutes at room temperature. In acetone, λmax=673 nm.

EXAMPLE 18

A 6.81 g quantity of isopropyl iodide was added to a solution prepared by mixing together 3.22 g of 2,3,3-trimethylindolenine and 2 ml of chloroform, and the mixture was heated in an antoclave at 80° C. for 4 hours. The precipitate resulting from the reaction was filtered off and washed with ether for isolation. The product was recrystallized from methanol, giving 3.35 g of 1-isopropyl-2,3,3-trimethylindolenium iodide in the form of purple crystals (yield 50%).

IR; 3050, 3000, 1590, 1480, 1140, 780 cm$^{-1}$.

EXAMPLE 19

To 3.85 g of 1-isopropyl-2,3,3-trimethylindolenium iodide was added 250 ml of 1.14N aqueous solution of potassium hydroxide, and the mixture was heated in a nitrogen atmosphere at 50° C. for 30 minutes. The reaction mixture was subjected to extraction with ether, and the extract was dried over magnesium sulfate and thereafter concentrated under reduced pressure, giving 1.88 g of 3,3-dimethyl-1-isopropyl-2-methyleneindoline in the form of an orange oily product (yield 83%).

$^1$H-NMR(CDCl$_3$); βppm 1.3(s, 6H, (CH$_3$)$_2$C<), 1.5(d, 6H, (CH$_3$)$_2$C—N), 3.9(d, 1H, vinyl), 3.9(d, 1H, vinyl), 4.1(m, 1H, CH—N), 6.4∼7.2(m, 4H, ArH).

EXAMPLE 20

In 130 ml of 2-butanone were dissolved 1.12 g of 3-methacryloxymethyl-5-nitrothiosalicylaldehyde and 0.80 g of 3,3-dimethyl-1-isopropyl-2-methyleneindoline. The solution was refluxed with heating in a nitrogen atmosphere for 5 hours. The solvent was distilled off from the reaction mixture under reduced pressure. The residue was purified in a silica gel column, giving 1.20 g of 3,3-dimethyl-1-isopropyl-8'-methacryloxymethyl-6'-nitrospiro-[indoline-2,2'(2'H)-1'-benzothiopyran] in the form of pale yellow crystals (yield 65%).

$^1$H-NMR(CDCl$_3$); δppm 1.13(s, 3H, CH$_3$C—Ar), 1.30(s, 3H, CH$_3$C—Ar), 1.42(d, 6H, (CH$_3$)$_2$C—N), 1.96(s, 3H, CH$_3$C=), 3.92(m, 1H, >CH—N), 5.16(dd, 2H, CH$_2$—O), 5.61(t, 1H, vinyl), 6.02(d, 1H, 3' or 4'-H), 6.17(s, 1H, vinyl), 6.71(d, 1H, 7-H), 6.80(t, 1H, 5-H), 6.89(d, 1H, 4'or 3'-H), 7.03(d, 1H, 4-H), 7.11(dt, 1H, 6-H), 8.00(d, 1H, 5'or 7'-H), 8.08(d, 1H, 7'or 5'-H).

IR; 2980, 2940, 1720, 1610, 1520, 1340, 1160, 750 cm$^{-1}$ MS(20 eV); 464(M+).

EXAMPLE 21

The compound obtained in Example 20 was dissolved in a solvent, and the solution was irradiated with ultraviolet rays in the same manner as in Example 17, whereby the solution, which was colorless and transparent, was changed to a green solution. The maximum absorption wavelength λmax was 581 nm in methanol, and 652 nm in acetone.

EXAMPLE 22

To the mixture of 2.87 g of 2,3,3-trimethylindolenine and 3 ml of chloroform was added 6.84 g of 1-iodooctadecane, and the mixture was heated in an autoclave at 80° C. for 4 days. Concentration of the reaction mixture gave red crystals, which, when washed with ether and dried, afforded 7.64 g of 1-octadecyl-2,3,3-trimethylindolenium iodide in the form of pink crystals (yield 79%).

$^1$H-NMR(CDCl$_3$); δppm 0.8(m, 3H, CH$_3$), 1.2(bs, 32H, —CH$_2$—), 1.7(s, 6H, (CH$_3$)$_2$C<), 3.1(s, 3H, CH$_3$C=), 4.6(m, 2H, CH$_2$—N), 7.2∼7.5(m, 4H, ArH).

EXAMPLE 23

In 30 ml of 2-butanone were dissolved 0.84 g of 8'-methacryloxymethyl-5-nitrosalicylaldehyde and 1.61 g of 1-octadecyl-2,3,3-trimethylindolenium iodide. A solution of 0.26 g of piperidine in 8 ml of 2-butanone was added to the solution in a nitrogen atmosphere. The mixture was heated at 80° C. for 2 hours and then concentrated under reduced pressure, giving 3.1 g of a viscous oily product. Purification of the product with a silica gel column afforded 1.21 g of 3,3-dimethyl-8'-methacryloxymethyl-6'-nitro-1-octadecylspiro[indoline-2,2'(2'H)-1'-benzothiopyran] in the form of a pale yellow oily product (yield 60%).

$^1$H-NMR(CDCl$_3$); δppm 0.68(m, 3H, CH$_3$), 1.21(s, 3H, CH$_3$C—Ar), 1.25(s, 30H, CH$_2$), 1.34(s, 3H, CH$_3$C—Ar), 1.65(m, 2H, CH$_2$), 1.96(s, 3H, CH$_3$—C=), 3.02(m, 1H, CH$_2$N), 3.27(m, 1H, CH$_2$N), 5.08(d, 1H, CH$_2$O), 5.61(t, 1H, vinyl), 6.03(d, 1H, 3' or 4'-H), 6.16(s, 1H, vinyl), 6.53(d, 1H, 7-H), 6.85(t, 1H, 5-H), 6.90(d, 1H, 4' or 3'-H), 7.05(d, 1H, 4-H), 7.16(t, 1H, 6-H), 7.98(d, 1H, 5' or 7'-H), 8.07(d, 1H, 7' or 5'-H), IR; 2930, 2860, 1720, 1605, 1515, 1340, 1155, 745cm$^{-1}$.

MS(20 eV); 674(M+).

EXAMPLE 24

When the compound obtained in Example 23 was dissolved in a solvent and then irradiated at room temperature with ultraviolet rays in the same manner as in Example 17, the solution which was colorless and transparent changed to a green solution. The maximum absorption wavelength λmax was 590 nm in methanol and 662 nm in acetone.

EXAMPLE 25

Into a reactor with the inside air replaced by nitrogen were placed 3.05 g of 5-methoxy-2,3-dimethylbenzoselenazolenium p-toluenesulfonate and 2.09 g of 3-methacryloxymethyl-5-nitrothiosalicylaldehyde, to which 300 ml of 2-butanone was added. The mixture was stirred on an ice bath in the dark. A solution of 0.72 g of piperidine in 100 ml of 2-butanone was slowly added to the mixture, followed by stirring on the ice bath for 4 hours and further by stirring at room temperature for 24 hours. The reaction mixture was concentrated under reduced pressure, 300 ml of methanol added to the residue, and the mixture stirred. The resulting precipitate was filtered off, washed with methanol and dried, giving 2.09 g of 8'-methacryloxymethyl-5-methoxy-3-methyl-6'-nitrospiro[benzoselenazoline-2,2'(2'H)-1'-benzothiopyran] (yield 56%).

MS(70 eV); 504(M+)

IR(KBr); 1721, 1637, 1585, 1521, 1340cm$^{-1}$, $^1$H-NMR(CDCl$_3$); δppm 1.95(s, 3H, CH$_3$—C=), 3.82(s, 3H, CH$_3$N), 3.84(s, 3H, CH$_3$O), 5.20(s, 2H, CH$_2$), 5.66(s, 1H, vinyl), 6.22(s, 1H, vinyl), 7.04(d, 1H, 3' or 4'-H), 8.09(d, 1H, 4' or 3'-H), 7.1∼8.8(5H, Ar—H).

The chloroform solution of the product was red at room temperature (23° C.), and λmax was 599 nm. When the solution was irradiated with visible light using an extra-high pressure mercury lamp equipped with a cutoff filter for passing visible light of longer wavelength than 500 nm, the solution became colorless and transparent with disappearance of the maximum absorption peak. When maintained at room temperature (23° C.), the colorless solution reverted to the original red solution. Further when the product was tested by two methods of repeating recoloration and photo erasure in the same manner as in Example 5, the product exhibited high reproducibility similarly without any decrease in absorbance.

Industrial Applicability

The spiropyran compound of the present invention itself is usable as a material such as recording material, photosensitive material, optical filter or decorative material. The present compound can further be homopolymerized or copolymerized with other polymerizable compound into a high polymer spiropyran compound for application to optical devices or dynamic devices.

I claim:

1. A spiropyran compound represented by the formula

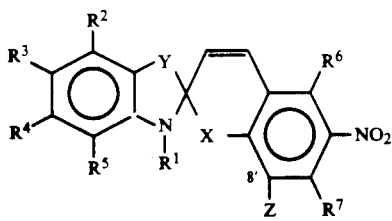

wherein R$^1$ is alkyl having 1 to 20 carbon atoms or aralkyl, R$^2$, R$^3$, R$^4$ and R$^5$ are the same or different and are each a hydrogen atom, alkyl having 1 to 6 carbon atoms, aryl or aralkyl, alkoxyl having 1 to 5 carbon atoms, halogen atom, cyano, trichloromethyl, trifluoromethyl or nitro, R$^6$ and R$^7$ are the same or different and are each a hydrogen atom, alkyl having 1 to 6 carbon atoms, aryl or aralkyl, halogen atom, cyano or nitro, X is an oxygen atom or sulfur atom, Y is Se or (CH$_3$)$_2$C<, Z is

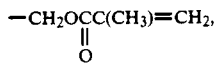

and X is a sulfur atom when Y is (CH$_3$)$_2$C<.

2. A compound according to claim 1, wherein Y is Se.

3. The compound according to claim 2, which is 8'-methacryloxymethyl-3-methyl-6'-nitro-1-selenaspiro-[2H-1'-benzopyran-2,2'-benzoselenenazoline].

4. The compound according to claim 2, which is 3-isopropyl-8'-methacryloxymethyl-5-methoxy-6'-nitro-1-selenaspiro[2H-1'-benzopyran-2,2'-benzoselenazoline].

5. The compound according to claim 2, which is 3-isopropyl-8'-methacryloxymethyl-5-methoxy-6'-nitro-1-selenaspiro[2H-1'-benzopyran-2,2'-benzoselenazoline].

6. The compound according to claim 2, which is 8'-methacryloxymethyl-5-methoxy-2-methyl-6'-nitro-1-selenaspiro[2H-1'-benzopyran-2,2'-benzoselenazoline].

7. The compound according to claim 2, which is 2,5-dimethyl-8'-methacryloxymethyl-6'-nitro-1-selenaspiro[2H-1'-benzopyran-2,2'-benzoselenazoline].

8. The compound according to claim 2, which is 8'-methacryloxymethyl-5-methoxy-3-methyl-6'-nitrospiro[benzoselenazoline-2,2'(2'H)-1'-benzothiopyran].

9. A compound according to claim 1, wherein Y is (CH$_3$)$_2$C<.

10. The compound according to claim 9, which is 8-methacryloxymethyl-6-nitro-1',3',3'-trimethyl-spiro[2H-1-benzothiopyran-2,2'-indoline].

11. The compound according to claim 9, which is 3,3-dimethyl-1-isopropyl-8'-methacryloxymethyl-6'-nitrospiro-[indoline-2,2'(2'H)-1'-benzothiopyran].

12. The compound according to claim 9, which is 3,3-dimethyl-8'-methacryloxymethyl-6'-nitro-1-octadecylspiro[indoline-2,2'(2'H)-1'-benzothiopyran].

* * * * *